United States Patent [19]

Powell et al.

[11] 4,336,334

[45] Jun. 22, 1982

[54] MICROBIOLOGICAL PROCESS FOR THE PRODUCTION OF POLY(β-HYDROXYBUTYRIC ACID)

[75] Inventors: Keith A. Powell, Yarm; Barbara A. Collinson, Peterlee, both of England

[73] Assignee: Imperial Chemical Industries Limited, London, England

[21] Appl. No.: 123,354

[22] Filed: Feb. 21, 1980

[30] Foreign Application Priority Data

Feb. 21, 1979 [GB] United Kingdom ................ 7906078

[51] Int. Cl.³ .......................... C12N 1/32; C12N 1/38; C12P 7/42
[52] U.S. Cl. .................................... 435/146; 435/244; 435/247
[58] Field of Search ............... 435/146, 142, 141, 136, 435/132, 244, 247, 135

[56] References Cited

U.S. PATENT DOCUMENTS

| | | | |
|---|---|---|---|
| 3,044,942 | 7/1962 | Baptist | 435/146 |
| 4,140,741 | 2/1979 | Lafferty et al. | 435/146 |
| 4,211,846 | 7/1980 | Lafferty | 435/141 |

OTHER PUBLICATIONS

Patt T. E., Cole G. C. and Hanson R. S., (1976), "Methylobacterium, A New Genus of Facultatively Methylotrophic Bacteria", Int. J. of Systematic Bacteriology, 26, 226–229.

O'Connor M., Wopat A. & Hanson R. S., (1977), "Genetic Transformation in *Methylobacterium organophilum*", J. of General Microbiology, 98, 265–272.

Gottschalk G.; *Bacterial Metabolism*, Springer–Verlag, ©1979, pp. 107, 108.

Lamanna C., and Mallette M. F.; *Basic Bacteriology*, Williams and Wilkins Co., 1965, pp. 225 and 532.

Patt et al.; *J. Bacteriology*, Nov. 1974, 120, No. 2, pp. 955–964.

O'Connor et al.; *J. Gen. Microbiology*, 1977, 101, pp. 327–332.

*Primary Examiner*—Raymond N. Jones
*Assistant Examiner*—Elizabeth J. Curtin
*Attorney, Agent, or Firm*—Cushman, Darby & Cushman

[57] ABSTRACT

Poly beta hydroxybutyric acid is produced by the aerobic culture of Methylobacterium organophilum strains NCIB 11482 to 11488 inclusive on a carbon source such as methanol.

6 Claims, No Drawings

MICROBIOLOGICAL PROCESS FOR THE PRODUCTION OF POLY(β-HYDROXYBUTYRIC ACID)

This invention relates to a microbiological process for the production of poly(β-hydroxybutyric acid), hereinafter referred to as PHB, and to micro-organisms for use in such a process.

It has been known since the 1920's that many bacteria are capable of accumulating PHB granules within their cells as an energy reserve material. Some of the bacteria, mainly naturally occurring, so capable are surveyed by Senior et al. in Advances in Microbial Physiology 1973, 10, 203–266. In that survey, it is reported that certain bacteria, notably *Azotobacter beijerinckii* and *Hydrogenomonas eutropha* could, under certain conditions, accumulate relatively high proportions of PHB. However such bacteria do not metabolise methanol which is a relatively cheap source of carbon.

It is known that certain bacteria that are capable of metabolising methanol, do, under certain conditions, metabolise methanol to PHB. Thus in our British Pat. No. 1,370,892 it is disclosed that certain strains of *Hyphomicrobium variabile* and *Pseudomonas rosea* accumulate PHB when grown on a methanol substrate. Furthermore it is disclosed by O'Connor et al. in J. General Microbiology 1977, 98, 265–272 that a mutant of *Methylobacterium organophilum* accumulates PHB when metabolising methanol but will only grow in the presence of glutamate. Pseudomonas AM1 is also known to metabolise methanol to PHB.

None of these known methanol-metabolising bacteria give sufficiently high yields of PHB of high molecular weight to render their use in the manufacture of PHB a commercial proposition. While Pseudomonas AM1 may, under favourable conditions give PHB contents of the order of 25% by weight or more, the molecular weight of the PHB so produced is relatively low.

We have now found certain strains of *Methylobacterium organophilum* that will metabolise methanol to give relatively high proportions of high molecular weight PHB.

Accordingly we provide a method of producing PHB comprising aerobically culturing a purified *Methylobacterium organophilum* micro-organism strain selected from strains designated by NCIB Nos. 11482 to 11488 inclusive and mutants and variants of such strains.

The NCIB Nos. are the numbers designated to specimen cultures of the strains deposited on Jan. 9, 1979 with the National Collection of Industrial Bacteria, Tory Research Station, Aberdeen, Scotland. Specimen cultures have also been deposited on at the Central Bureau Voor Schimmelcultures, Baarn, Netherlands and have been designated by the following CBS numbers

| NCIB No | CBS No |
|---------|--------|
| 11482 | 137.80 |
| 11483 | 138.80 |
| 11484 | 139.90 |
| 11485 | 140.80 |
| 11486 | 141.80 |
| 11487 | 142.80 |
| 11488 | 143.80 |

Further in accordance with the invention, we provide a pure culture of a *Methylobacterium organophilum* strain selected from strains designated by NCIB Nos. 11482 to 11488 inclusive and mutants and variants of such strains.

DESCRIPTION OF THE NOVEL STRAINS

1. General

The novel strains are very similar to one another and are short Gram negative motile rods of approximate size 2 μm × 0.5 μm, with some variation in thickness. Occasionally branched rods may be observed. Under certain conditions they contain granules of poly(β-hydroxybutyric acid). They do not form spores.

When grown aerobically on methanol agar the organism is in the form of pink pigmented, transparent, circular, entire, convex, smooth, shiny colonies. The pigment is not water soluble and has a spectrum and solubility corresponding to the carotenoids. When incubated anaerobically on the same medium no pigment is produced and flat, white, diffuse colonies are obtained. Similar amounts of growth are obtained when grown aerobically or anaerobically. Hereinafter all tests refer to aerobic cultures.

The organisms sometimes produce two colony types in the form of large and small colonies. When small colonies were picked off and streaked on to methanol agar, only small colony types grew up. Likewise when large colony types were picked off and streaked on to methanol agar only large colonies grew. Another type of colony, the flat white colony, was sometimes observed in fermenter cultures and was similar to the colony type observed using anaerobic growth and presumably results from occasional conditions of oxygen limitation in the fermenters. No taxonomic differences were found between the different colony types.

In the following sections, standard taxonomic tests were performed with incubation at 37° C. except where noted. Where the test requires a minimal medium, this had the following elemental composition, expressed in mg $l^{-1}$:

| | | |
|---|---|---|
| nitrogen | 380 | supplied as $(NH_4)_2 SO_4$ |
| phosphorus | 620 | supplied as $K_2HPO_4$ |
| potassium | 780 | and |
| sodium | 230 | $Na H_2PO_4 . 2H_2O$ |
| magnesium | 20 | supplied as $MgSO_4 . 7H_2O$ |
| calcium | 0.7 | supplied as $CaCl_2$ |
| iron | 0.2 | supplied as $FeCl_3 . 6H_2O$ |
| manganese | 0.025 | supplied |
| zinc | 0.025 | as |
| copper | 0.005 | sulphates |
| sulphur | 460 | supplied by the sulphates |

2. Growth on various media 48 hours at 37° C. (unless indicated to the contrary)

A. Solid media

| | | | Colony description* | | | |
|---|---|---|---|---|---|---|
| medium | growth | pigment | transparent | smooth | shiny | size mm |
| nutrient agar plates | ✓ | pink | | ✓ | ✓ | 0.5–1 |
| nutrient agar slopes | ✓ | pink | | ✓ | ✓ | 0.5–1 |
| nutrient gelatin | ✓ ** | pink | | ✓ | ✓ | 0.5–1 |
| methanol/salts agar (0.1% v/v) | ✓ | pale pink | ✓ | ✓ | ✓ | 0.5–1.5 |

-continued

| medium | growth | pigment | Colony description* transparent | smooth | shiny | size mm |
|---|---|---|---|---|---|---|
| methanol)+ | | | | | | |
| methanol/salts agar (0.5% v/v methanol) | ✓ | pink | ✓ | ✓ | ✓ | 0.5–1 |
| starch agar | x | | | | | |
| oatmeal agar | ✓ | very pale pink | x | ✓ | | 0.1–0.5 |
| tyrosine agar | ✓ | pink | ✓ | ✓ | ✓ | 1–1.5≠ 0.5–0.7 |
| glycerol/asparagine agar | ✓ | bright pink | ✓ | | ✓ | 0.5–1 |
| glucose/asparagine | ✓ | pink | ✓ | ✓ | ✓ | 1.5–2 |
| yeast malt agar | ✓ | pink | ✓ | | ✓ | 1.5–2 |

*all colonies were circular, entire, and convex
**no liquefaction of the gelatin occured
+incubated at 30° C.
≠two distinct colony types

B. Liquid media

| | |
|---|---|
| Nutrient broth | Moderate growth, uniform, no flocculation or formation of a ring or pellicle |
| Litmus milk | No growth; no clotting or acid production |
| Methanol broth 0.5% v/v methanol 24 hours | Scanty growth; formation of a ring which disintegrates on shaking. Turbidity variable. Uniform/Flocculant. Deposit - Flocculant at times disintegrates on shaking. |
| Methanol broth 0.5% v/v methanol 48 hours | As 24 hour culture but growth is profuse. |

The different strains gave similar results: the only difference noticeable being that with strain NCIB 11483, the colouration was deeper.

3. Growth at various temperatures (48 hours, minimal salts medium +0.5% v/v methanol, pH 6.8)

| Temperature °C. | Growth (all novel strains) |
|---|---|
| 4 | no |
| 10 | no |
| 15 | yes |
| 23 | yes |
| 30 | yes |
| 37 | yes |
| 40 | yes |
| 42 | slight |
| 45 | no |

4. Growth at various values of pH (48 hours, minimal salts medium +0.5% v/v methanol, 37° C.)

| pH | Growth (all novel strains) |
|---|---|
| 1 | no |
| 2 | slight |
| 3 | yes |
| 4 | yes |
| 5 | yes |
| 6 | yes |
| 7 | yes |
| 8 | yes |
| 9 | yes |
| 10 | yes |
| 11 | slight |
| 12 | no |
| 13 | no |

5. Standard Taxonomic tests (P=positive, N=negative, D=doubtful; results the same for all novel strains)

| | |
|---|---|
| catalase | P |
| oxidase | D |
| O-F glucose | growth, no indicator change |
| acid fastness | not acid fast |
| MR & VP | both N |
| reduction of nitrate | N |
| denitrification | P |
| indole production | N |
| H$_2$S production | N |
| coagulase | N |
| urease | P |
| haemolysis | N |
| lipase | N |
| phosphatase | N |
| motility (microscopic examination) (agar medium) | P (by polar flagella) P |
| pectinase | N |
| utilisation of citrate | N |
| utilisation of malonate | N |
| deamination of phenylalanine | P |
| utilisation of inorganic nitrogen | P |
| decarboxylation of L-lysine hydrochloride | N |
| L-arginine hydrochloride | P |
| L-ornithine hydrochloride | N |
| hydrolysis of lecithin | N |
| Tween 20 | N |
| Tween 80 | N |
| arginine | N |
| starch | N |
| hippurate | N |
| growth on carbohydrates* | |
| L-arabinose | N |
| D-xylose | N |
| D-glucose | P |
| D-mannose | P |
| D-fructose | P |
| D-galactose | N |
| maltose | N |
| sucrose | N |
| lactose | N |
| D-sorbitol | P |
| D-mannitol | N |
| trehalose | N |
| inositol | P |
| glycerin | P |
| starch | N |

*in all cases there was no acid or gas production.

| | |
|---|---|
| oxidation of ethanol | P |
| resistance to potassium cyanide | not resistant |
| sodium chloride | tolerates 6.5% by weight solution |
| temperature minimal media + methanol | will grow after heating to 60° C. for 2 hours |
| nutrient agar | will grow after heating to 60° C. for 2 hours |
| penicillin G | resistant |
| streptomycin | sensitive |
| chloramphenicol | resistant |

| | -continued | |
|---|---|---|
| tetracycline | sensitive | |
| novobiocin | sensitive | |
| polymyxin B | resistant. | |

6. Comparison with known similar micro-organisms

The novel strains were also compared with *Methylobacterium organophilum* (ATCC 27886) and Pseudomonas AM1 (NCIB 11489).

(ATCC No. refers to the number designated by the American Type Culture Collection, 12301 Park Lawn Drive, Rockville, Md. 20852, USA).

In the following table data has been selected to demonstrate the main differences between the novel strains and the known micro-organisms. In these tests, incubations were performed at 30° C.

| | Strains NCIB 11482–8 | Ps AM1 NCIB 11489 | M. Organophilum ATCC 27886 |
|---|---|---|---|
| Growth on methane | P | N | P |
| Growth on methane after period of growth on methanol | P | N | N |
| Growth at 10° C. on methanol | N | P | N |

Thus one distinction between the M. organophilum strains of the present invention and the known strain (ATCC 27886) is in relation to their metabolism of methanol and methane. Thus with the known strain (ATCC 27886) the capability of metabolising methane is lost after culturing the strain on methanol: ie after growing the strain on methanol it will not then grow using methane as the carbon source. In contrast thereto, the strains of the present invention are still capable of utilising and growing on methane as the carbon source after a period of growth on the methanol. The most noticeable differences among the strains NCIB 11482–11488 were that when fermented under identical conditions, the amount of PHB accumulated varied slightly from strain to strain.

The micro-organisms were obtained from the drains of a methanol producing industrial plant and selected by growing on an aqueous methanol medium followed by culturing in the absence of any carbon source for several days. Surviving strains were isolated and purified by conventional techniques.

Mutants of the strains may be produced by conventional techniques, for example by exposure of the strains to UV radiation or by exposure to mutant inducing chemicals such as ethane/methane sulphonate or N-methyl-N-nitro-N-nitrosoguanidine. Mutants so produced can be separated from the wild-type strains by known techniques eg penicillin and cycloserine enrichment techniques.

Production of PHB

As indicated above, the micro-organisms metabolise methanol. However they are also capable of metabolising other carbon sources containing carbon-hydrogen bonds. Hydrocarbons can be metabolised, even methane in spite of its inertness. Oxygenated hydrocarbons, such as alcohols, ethers, carboxylic acids, and esters may be metabolised. Amines, for example trimethylamine, may be metabolised but, as will be explained hereinafter, will not give appreciable PHB concentrations when used as the sole carbon source, unless the accumulation of PHB is conducted under phosphorus starvation conditions, because of the need to maintain nitrogen and/or phosphorus starvation conditions for PHB accumulation. Carbohydrates may also be metabolised. For the production of PHB therefore, the assimilable carbon source should preferably be free of nitrogen.

While the present invention is primarily concerned with the use of the micro-organisms to metabolise methanol, the present invention also embraces the micro-organisms themselves when aerobically cultured on an aqueous solution of a assimilable carbon source, and also embraces the use of the micro-organisms to metabolise other carbon sources, for example those set out above.

In addition to the assimilable carbon source, sources of assimilable nitrogen and phosphorus are required for growth of the micro-organism. These may conveniently be an ammonium salt, eg sulphate or chloride, and a phosphate, eg sodium dihydrogen phosphate. An ammonium phosphate may be used as the source of both nitrogen and phosphorus, but, as indicated hereinafter, in view of the differing levels of nitrogen and phosphorus required, to avoid too great an excess of phosphorus, an ammonium phosphate is preferably used in admixture with another ammonium compound.

It has been found that PHB accumulation is favoured by culturing the micro-organism under nitrogen and/or phosphorus starvation conditions. In a preferred process, the micro-organism is first grown in an aqueous medium containing sources of assimilable nitrogen and phosphorus and then culturing is continued under nitrogen and/or phosphorus starvation conditions. During the first stage the micro-organism grows, ie multiplies, to give an economic concentration of the micro-organism. Durng this stage, ie while the micro-organism is not starved of either nitrogen or phosphorus, the micro-organism will accumulate little or no PHB, and, at the end of the first stage, it will be substantially free of PHB.

In the first stage the micro-organism is preferably grown to a concentration of at least 5, preferably 10 to 30, and particularly 20 to 25 g $l^{-1}$. The micro-organism, when grown under conditions that are not starved of nitrogen or phosphorus so that little or no storage products eg PHB are accumulated therein, contains about 8 to 12% by weight of nitrogen and 1.0 to 2% by weight of phosphorus. The amount of assimilable nitrogen and phosphorus sources should be sufficient to support the desired weight of biomass produced in the first stage without becoming the limiting nutrient. Hence to achieve a biomass concentration of 20 g $l^{-1}$ in the first stage, a concentration of at least about 1.6 to 2.4 g $l^{-1}$ of assimilable nitrogen and of at least about 200 to 400 mg $l^{-1}$ of assimilable phosphorus is required if phosphorus or nitrogen is not to become the limiting nutrient in the first stage. It is preferred that the first stage is conducted under conditions such that, when the desired first stage biomass concentration has been achieved, there is not present a substantial excess of the nutrient, ie nitrogen and/or phosphorus, of which the micro-organism is to be starved in the second stage. Where the micro-organism is starved of only one of these nutrients, nitrogen and phosphorus, in the second stage, it will be appreciated that an excess of the other nutrient may be present at the end of the first stage. In general the concentrations of nitrogen and phosphorus sources in the first stage will be within the ranges 0.5 to 5 g $l^{-1}$ of assimilable nitrogen and 50 to 2500 mg $l^{-1}$ of assimilable phosphorus respectively, depending on the desired first stage biomass concentration. The amount of assimilable phosphorus in the first stage is preferably less than 750 mg $l^{-1}$, particularly where phosphorus starvation conditions are used in the second stage.

The first stage is preferably conducted under carbon source, eg methanol, limitation conditions to obtain efficient conversion of the carbon source. Preferably the conditions are such that the micro-organism grows, ie reproduces at, or near to, its maximum rate. The first stage is preferably operated under conditions such that the average rate of increase in biomass is at least 1 g$l^{-1}$ $hr^{-1}$. By the term average rate of increase in biomass we mean the total increase in biomass during the first stage divided by the first stage growth time. (In a batch process there may be a "lag" stage initially during which no growth occurs. In computing the first stage growth time, any such "lag" time is subtracted from the overall time of the first stage).

As mentioned above, the accumulation of PHB is favoured by conducting the second stage under nitrogen and/or phosphorus conditions. Thus in the second stage the micro-organism is starved of nitrogen or phosphorus or both nitrogen and phosphorus. The nutrient of which the micro-organism is starved is hereinafter referred to as the depleted nutrient. Under nitrogen and/or phosphorus starvation condition, little or no growth, ie reproduction, of the micro-organism occurs, and so the biomass increases as a result of metabolism of the carbon source to non-proteinaceous material, mainly PHB. To achieve this, the aqueous medium in the second stage should contain little or no source of assimilable depleted nutrient. However a source of a small amount of the depleted nutrient may inevitably be present in the second stage, particularly where a continuous process is utilised as some of the depleted nutrient present in the aqueous medium from the first stage may be carried forward to the second stage. Also, we do not preclude the addition of a small amount, eg up to 1 g $l^{-1}$ in the case of nitrogen and up to 200 mg $l^{-1}$ in the case of phosphorus, of the depleted nutrient in the second stage which may, in some cases, be desirable to obtain efficient conversion of the carbon source to PHB.

Accordingly, by the term nitrogen and/or phosphorus starvation, as used herein, we mean that the amount, if any, of a source of the depleted nutrient (ie nitrogen, phosphorus, or nitrogen and phosphorus) present in the second stage is such that the PHB in the final product amounts to at least 30%, preferably at least 70%, by weight of the increase in biomass in the second stage.

It will be appreciated that, where the second stage is conducted under conditions of starvation of only one of nutrients nitrogen and phosphorus, the other of said nutrients may be present in conventional quantities.

The second stage is conducted for such a time that the biomass is increased, mainly by synthesis of PHB, by at least 30%, preferably by at least 50% by weight. Preferably the two stages are operated so that the first stage produces a suspension having a biomass concentration of 20 to 25 g $l^{-1}$ and this biomass is increased in the second stage to a biomass concentration of 33 to 55 g $l^{-1}$.

To avoid the accumulation of storage materials, eg carbohydrates, other than PHB, the second stage is preferably operated under carbon limitation.

The conditions in the second stage are preferably such that the average rate of PHB accumulation is at least 0.02 $hr^{-1}$, and in particular at least 0.04 $hr^{-1}$. By the term average rate of PHB accumulation we mean the amount of PHB accumulated in the second stage divided by the product of the second stage time and the difference between the final biomass and the amount of PHB accumulated.

As is known in the art other elements, some in trace quantities, are necessary for growth of the micro-organism. For the strains in accordance with the invention, typical concentration ranges in mg $l^{-1}$ of such elements in assimilable form are as follows:

| | |
|---|---|
| S | 50–1500 |
| K | 50–1000 |
| Na | 10–500 |
| Mg | 10–200 |
| Ca | 1–25 |
| Fe | 1–20 |
| Mn | 0.1–10 |
| Zn | 0.1–5 |
| Cu | 0.01–1 |

The carbon source, eg methanol, will generally be used at a concentration within the range 1 to 10% by volume of the aqueous medium.

The process may be operated under batch conditions: in this case PHB will be accumulated when the available nitrogen and/or phosphorus in the batch has been utilised. Ignoring any "lag" time before exponential growth of the micro-organism occurs, the PHB accumulation stage will generally take 0.5 to 2 times the length of the growth stage if economically high yields of PHB are to be obtained.

Alternatively the process may be operated on a continuous basis. Thus the first, growth, stage may be operated continuously in one vessel and the product thereof is continuously fed to a second vessel wherein the second, PHB accumulation, stage is conducted. The second stage may be operated on a continuous or a batch basis. Where a batch second stage is used a series of batch vessels are employed with one or more being filled with the product from the first stage vessel while the second stage is being conducted in one or more of the other second stage vessels.

Where the process is operated on a continuous basis, the growth stage is preferably operated at a dilution rate of 0.1 to 0.25 $hr^{-1}$ (dilution rate is the reciprocal of the average residence time). If the second stage is also continuous, as is preferred, the dilution rate is preferably 0.05 to 0.15 $hr^{-1}$.

When operated on a continuous basis, the amount of the depleted nutrient source utilised in the first stage is preferably only just sufficient to support the biomass obtained in the first stage so that there is little or no depleted nutrient source available in the cell suspension transferred to the second stage of the process. Preferably the only source of depleted nutrient in the second stage is the depleted nutrient, if any, present in the aqueous medium transferred from the first stage.

The micro-organisms are preferably cultured at a temperature in the range 25° to 42° C., the optimum temperature being about 37° C.

The micro-organism is cultured aerobically, preferably at a dissolved oxygen tension between 20 and 80% of air saturation.

The pH of the aqueous medium is preferably maintained within the range 6 to 8 and is preferably above 6.5. The pH may be controlled in known manner: generally small additions of a base are required to maintain optimum pH. Ammonia may be used to control pH unless nitrogen starvation conditions are used in the PHB accumulation stage, in which case it is preferred to control pH by addition of a non-nitrogeneous base, eg sodium hydroxide.

The PHB is produced as granules inside the microorganism cells. While the bacterial cells containing PHB may themselves be used as a moulding material, for example as described in U.S. Pat. No. 3,107,172, it is generally desirable to separate the PHB from the bacterial cells. This may be done by subjecting the cells to a cell breakage step followed by extraction of the PHB with a suitable solvent. The cells may be broken by shearing, for example by homogenisation, bead milling, roller milling, or French pressing, the cell suspension. Other methods of cell disruption include osmotic shock, sonic or ultra-sonic vibration, and enzymic cell wall lysis. Treatment with hypochlorite to destroy the bacterial cell membrane chemically could be used but preferably is not because it usually causes severe degradation of the PHB therein.

Another method of effecting cell disruption is by spray drying the aqueous suspension of the bacterial cells, leaving dried cells from which the PHB can be extracted by a suitable solvent.

Preferred solvents for extracting the PHB from the disrupted cells include partially halogenated hydrocarbons such as chloroform, dichloromethane, 1,2-dichloroethane and 1,2-dichloropropane. 1,2-Dichloroethane is the most preferred solvent.

Where the PHB is extracted by contact of the solvent with an aqueous suspension of the disrupted cells, for efficient separation of the PHB, the cell suspension preferably has a concentration of 5 to 15% by weight biomass solids. The cell suspension is preferably concentrated, eg by centrifugation, to within this range where this is necessary (the cell suspension as produced in the second stage may already have a concentration within this range: however even in such cases some concentration may be desirable). The solvent is preferably contacted with the cell suspension at 10° to 40° C. The amount of solvent used is preferably 1 to 4 times the volume of the cell suspension. Separation of the solvent and aqueous phases in favourable conditions takes place under natural gravity but in some cases it may be necessary to utilise a centrifuge. To avoid formation of a stable emulsion of the PHB-containing solvent and the aqueous phase, the pH of the aqueous cell suspension may be adjusted to, or near to, the isoelectric point of the disrupted cells prior to contacting with the solvent.

Where the PHB is extracted from dried cells, ie by contact of the solvent with cells after a suspension thereof has been spray dried, the dried cells are preferably subjected to a preliminary extraction with a PHB-non solvent eg acetone or methanol, to extract pigment and lipids from the cells, prior to contact with the PHB extraction solvent. This preliminary extraction is preferably performed under reflux.

Where the cells are subject to such a preliminary lipid and pigment extraction, the PHB is preferably extracted by contact with the extraction solvent at above 40° C., eg under reflux conditions.

After contacting the disrupted cells with the PHB extraction solvent, the PHB-containing solvent phase is separated from the cell debris, eg by separation of the aqueous and solvent phases, where the PHB is extracted from an aqueous suspension of the cells, or by filtration where the PHB is extracted from dried cells. After separation of the PHB-containing solvent phase from the cell debris, the solution is preferably filtered to remove any suspended small bacterial fragments. Such filtration is preferably conducted using a filter, eg a glass fibre filter, having a pore size of less than 5 $\mu$m, preferably less than 2 $\mu$m.

The separated PHB-containing solution may be used directly (preferably after filtration) for making solvent cast articles such as coatings, films, or fibres, or the solution can be treated further to separate solid PHB, for example by evaporation or by precipitation by addition of the PHB-containing solvent to a liquid in which PHB is insoluble and with which the solvent is mixible. Examples of suitable liquids include petroleum ether and methanol/water mixtures. The PHB may be purified, if desired, by washing with methanol or acetone.

After extraction of the PHB, the bacterial cell residue may be worked up for use as a feedstuff or fertiliser.

The invention is illustrated by the following examples in which all percentages are expressed by weight.

EXAMPLE 1

An inoculum of *Methylobacterium organophilum* strain NCIB 11483 is grown aerobically for 48 hours at 37° C. in an aqueous medium of pH 6.8 in a shake flask. The aqueous medium used was the minimal salts medium, as used in the taxonimic study reported hereinbefore, with the addition of 5 ml $1^{-1}$ methanol.

250 ml of the resulting starter culture was then added to a fermenter containing 5 l of an aqueous medium containing 10 ml $1^{-1}$ methanol and minerals to give the following elemental composition (expressed in mg $1^{-1}$)

| | |
|---|---|
| S | 1300 |
| N | 1060 |
| P | 620 |
| K | 100 |
| Mg | 40 |
| Ca | 21 |
| Fe | 3 |
| Mn | 0.75 |
| Zn | 0.7 |
| Cu | 0.15 |

The culture was grown aerobically at 37° C. and at a pH 6.8. pH was controlled by addition of 2 M NaOH solution. The lag time was about 8 hours. After 24 hours methanol was added continuously at a rate of 8 g hr$^{-1}$. After a further 8 hours the culture entered nitrogen depletion condition. At this stage the biomass dry weight was 12 g $1^{-1}$. After a further 20 hours the biomass dry weight had increased to 20 g $1^{-1}$ and the PHB content of the biomass was 40%.

The resulting cell suspension was concentrated by centrifugation to a cell cream containing 8% biomass solids. The cells were then disrupted by milling in a Dynomill at a throughput of 15 l hr$^{-1}$ at an inlet temperature of 20° C. and an outlet temperature of 40° C.

500 ml of the milled cell cream was then mixed with 1 l of 1,2-dichloroethane at 20° C. and blended for 10 minutes by means of a Silverson (RTM) blender model L2R. Owing to energy dissipation the temperature rose to 40° C. The resulting emulsion was cooled and then centrifuged at 13000 g for 15 minutes at 15° C. The upper layer of aqueous solution and cell debris was decanted off. The lower layer, PHB dissolved in 1,2-dichloroethane, was poured slowly with vigorous stirring into 5 l of a methanol/water mixture (4 vols. methanol:1 volume water). The precipitate was collected on a filter, washed 5 times with 1 liter of methanol until white, and dried in vacuo at 50° C. The resulting polymer had a purity of 99.5% and a weight average molecular weight (as measured by gel permeation chromatography) of 270,000 and a number average molecular weight (as measured by a ratio isotope labelling method) of 150,000.

EXAMPLE 2 (Comparative)

A similar fermentation to that of Example 1 was performed at pH 7.0 and a temperature of 30° C. using Pseudomonas AM1 (NCIB 11489). The biomass dry weight obtained was 13 g $l^{-1}$ with a PHB content of 35%.

On extraction as in Example 2, the PHB was found to have a weight average molecular weight of only 40–50,000.

EXAMPLE 3

In order to compare the various strains of the invention, a series of experiments were performed using the various strains. A fresh plate culture of the strain was inoculated into a shake flask containing 50 ml of an aqueous medium A and the culture was grown aerobically for 18 hours at 37° C. The product was then centrifuged and the pellet obtained was resuspended in a shake flask containing 50 ml of an aqueous medium B and grown aerobically for 24 hours at 37° C. The product was then centrifuged, washed with methanol and then the PHB content assessed by an infra-red analysis technique. The infra-red analysis expresses the data as a ratio; the higher the ratio the greater the PHB content.

The results are shown in the following table.

| NCIB Strain | IR Ratio | Approx PHB content+ (%) |
|---|---|---|
| 11482 | 1.69 | 41 |
| 11483 | 1.87 | 47 |
| 11484 | 1.29 | 28 |
| 11485 | 1.16 | 23 |
| 11486 | 1.16 | 23 |
| 11487 | 1.49 | 34 |
| 11488 | 1.25 | 26 |
| Pseudomonas AM1* (11489) | 1.33 | 29 |

*cultured at 30° C., not 37° C., because this micro-organism does not grow well at 37° C.
+determined from a correlation of IR Ratio and PHB content established from larger scale experiments.

In this experiment medium B had the following composition, per liter of deionised water:

| | | |
|---|---|---|
| MgSO$_4$ . 7H$_2$O | 4 mg | |
| FeCl$_3$ . 6H$_2$O | 1 mg | |
| K$_2$HPO$_4$ | 1.9 g | } buffer at |
| NaH$_2$PO$_4$ . 2H$_2$O | 1.4 g | } pH 6.8 |
| Trace element solution | 1 ml | |
| Methanol | 0.5 ml. | |

The trace element solution had the following composition:

| | |
|---|---|
| CaCO$_3$ | 1.8 g/l |
| MnSO$_4$ . 4H$_2$O | 0.01 g/l |
| ZnSO$_4$ . 7H$_2$O | 0.01 g/l |
| CuSO$_4$ . 5H$_2$O | 0.02 g/l |
| 1M HCl | 36.6 ml/l |

Medium A was identical to medium B with the addition of 1.8 g/l (NH$_4$)$_2$SO$_4$.

EXAMPLE 4

Some of the strains utilised in Example 3 were further assessed by a larger scale fermentation.

3 l of an aqueous medium (medium C) was inoculated with 20 ml of a 48 hour starter culture which had previously been checked for purity. Medium C had the following composition, per liter of deionised water:

| | |
|---|---|
| MgSO$_4$ . 7H$_2$O | 0.8 g |
| K$_2$SO$_4$ | 0.45 g |
| (NH$_4$)$_2$SO$_4$ | 1 g |
| FeCl$_3$ . 6H$_2$O | 4 mg |
| 1.1M H$_3$PO$_4$ | 18 ml |
| Trace element solution | 20 ml |
| Methanol | 10 ml |

The trace element solution had the same composition as that used in Example 3.

During fermentation the pH was controlled at 6.8±0.2 by addition of 2 M NaOH and the temperature maintained at 37°±1° C. The dissolved oxygen tension was maintained at between 20 and 80% of air saturation. The methanol concentration was maintained in an excess by periodic methanol addition.

The lag period following inoculation was of the order of 10–15 hours and the subsequent exponential growth phase continued until the extra-cellular nitrogen source was depleted, usually after 25 to 30 hours from inoculation. The amount of nitrogen source was sufficient to support a total dry cell weight of about 2 g $l^{-1}$. Thereafter increase in biomass results mainly from PHB accumulation.

The micro-organism was harvested, generally after 60–75 hours from inoculation. The results are shown in the table.

| NCIB Strain | Cell weight g/l after 20 hr | Cell weight g/l after 40 hr | Cell weight g/l at harvest | Time of harvest hrs | % PHB in harvested product |
|---|---|---|---|---|---|
| 11483 | 1.1 | 5.0 | 5.1 | 87 | 39 |
| 11483 | 0.8 | 2.9 | 3.6 | 85 | 39 |
| 11483 | 0.8 | 3.2 | 3.2 | 73 | 41 |
| 11483 | 1.7 | 5.1 | 5.4 | 75 | 41 |
| 11484 | 1.5 | 4.1 | 4.1 | 65 | 29 |
| 11485 | NM | 4.2 | 5.3 | 88 | 41 |
| 11486 | NM | 3.8 | 5.1 | 68 | 36 |
| 11487 | NM | 3.2 | 4.1 | 48 | 35 |
| 11487 | 1.9 | 4.6 | 4.6 | 74 | 40 |
| Ps AM1* 11489 | 0.8 | 3.9 | 5.5 | 70 | 45 |

-continued

| NCIB Strain | Cell weight g/l after 20 hr | after 40 hr | Time of at harvest | harvest hrs | % PHB in harvested product |
|---|---|---|---|---|---|
| Ps AM1* 11489 | 0.9 | 4.5 | 6.0 | 72 | 46 |

*fermentation performed at 30° C.
NM = not measured.

It is seen that, while the times to harvest varied considerably, in most cases the biomass increased only by a little after 40 hours and the bulk of the PHB accumulation had, in most cases, occurred prior to 40 hours from inoculation.

EXAMPLE 5

Methylobacterium organophilum strain NCIB 11483 was continuously fermented aerobically at pH 6.8 at a temperature of 37° C. in an aqueous medium at a dilution rate of 0.15 hr$^{-1}$ in a fermenter containing approximately 1500 ml of the aqueous medium. The substrate, methanol, concentration was 21.4 g l$^{-1}$.

The medium contained mineral salts to give the following elemental composition (expressed in mg l$^{-1}$):

| S | 1410 |
|---|---|
| N | 1060 |
| P | 612 |
| K | 200 |
| Mg | 80 |
| Ca | 8.4 |
| MN | 0.3 |
| Zn | 0.3 |
| Cu | 0.06 |

Iron, as FeCl$_3$.6H$_2$O was incorporated as a solution in the methanol at a concentration of 0.16 mg Fe per ml methanol. pH control was by addition of 2 M NaOH.

The overflow from the fermenter was used as the feed, together with more methanol, to a second continuous fermenter wherein fermentation was continued at a dilution rate of 0.07 hr$^{-1}$. The methanol concentration in the second fermenter was 35 g l$^{-1}$. The temperature was again 37° C. and pH again controlled at 6.8 by NaOH addition. Steady state fermentation was conducted for 51 days before being terminated because of a minor mechanical failure.

The overflow from the first fermenter contained 8.9±0.5 g l$^{-1}$ of biomass (ie during the 51 days continuous operation the biomass concentration varied between 8.4 and 9.4 g l$^{-1}$ but averaged 8.9 g l$^{-1}$).

The average rate of increase in biomass in the first stage was thus 1.3 g l$^{-1}$ hr$^{-1}$ (biomass×dilution rate).

The amount of nitrogen present, 1060 mg l$^{-1}$, in the aqueous medium fed to the first fermenter is sufficient to support about 11 g l$^{-1}$ biomass and so the overflow fed to the second fermenter contained about 200 mg l$^{-1}$ of N.

The product obtained from the second fermenter contained 18.7±1.0 g l$^{-1}$ of biomass and the PHB content varied between 30 and 50%, average 40%, of the biomass dry weight.

The average amount of PHB accumulated in the second stage was thus about 7.5 g l$^{-1}$. The increase in biomass in the second stage as a result of PHB accumulation, was thus about 76% of the total biomass increase in the second state.

The average PHB accumulation rate in the second stage was about $$0.047 \text{ hr}^{-1} \frac{(\text{dilution rate} \times \text{amount PHB accumulated})}{(\text{total biomass} - \text{amount of PHB accumulated})}$$

The PHB could be isolated from the product of the second fermenter by the method described in Example 1.

EXAMPLE 6

Methylobacterium organophilum strain NCIB 11483 was continuously fermented aerobically at pH 6.8 at a temperature of 37° C. in an aqueous medium at a dilution rate of 0.15 hr$^{-1}$ in a fermenter containing approximately 1500 ml of the aqueous medium. The substrate, methanol, concentration was 21 g l$^{-1}$. The aqueous medium contained mineral salts to give the following elemental composition (expressed in mg l$^{-1}$):

| S | 200 |
|---|---|
| K | 200 |
| P | 102 |
| Mg | 80 |
| Na | 16 |
| Ca | 8.4 |
| Mn | 0.3 |
| Zn | 0.3 |
| Cu | 0.06 |

Iron, as FeCl$_3$.6H$_2$O, was incorporated as a solution in the methanol at a concentration of 0.16 mg Fe per ml methanol. pH control was by addition of an ammonia solution containing approx. 140 g l$^{-1}$ of ammonia, thereby ensuring an adequate supply of assimilable nitrogen.

The overflow, which contained 9.5 g l$^{-1}$ of micro-organism cells, from the fermenter was used as the feed together with more methanol, to a second continuous fermenter wherein fermentation was continued at a dilution rate of 0.095 hr$^{-1}$. The methanol concentration in the second fermenter was 57 g l$^{-1}$. The temperature was again 37° C. and pH was again controlled at 6.8 by addition of the ammonia solution. In this second fermenter the micro-organism thus had an ample supply of assimilable nitrogen but was starved of phosphorus.

The product obtained from the second fermenter contained 31.1 g l$^{-1}$ of micro-organism cells which contained about 25% PHB.

The PHB could be isolated from the product of the second fermenter by the method described in Example 1.

We claim:

1. A method of producing poly($\beta$-hydroxybutyric acid) comprising aerobically culturing a purified methylobacterium organophilum micro-organism strain selected from strains designated by NCIB Nos. 11482 to 11488 inclusive and those mutants and variants derived from said strains that are capable of accumulating poly($\beta$-hydroxybutyric acid) when grown on methanol as a carbon source.

2. A method according to claim 1 wherein the micro-organism is cultured in an aqueous medium under conditions of carbon source limitation.

3. A method according to claim 1 wherein the micro-organism is grown under continuous culture conditions.

4. A method according to claim 1 wherein, after culturing the micro-organism the poly($\beta$-hydroxybutyric acid) is separated from the micro-organism.

5. A method of producing poly(β-hydroxybutyric acid) comprising aerobically culturing a purified methylobacterium organophilum micro-organism strain selected from strains designated by NCIB Nos. 11482 to 11488 inclusive and mutants and variants of said strains capable of utilizing the growing on methane as the carbon source after a period of growth on methanol.

6. A method
(a) the microorganism is continuously cultured in a first vessel to a first concentration in the presence of sufficient assimilable nitrogen and phosphorus to support the growth of said micro-organism to said concentration without substantial accumulation of poly(β-hydroxybutyric acid);
(b) continuously feeding the culture produced in said first vessel to a second vessel; and
(c) continuously culturing said micro-organism in said second vessel to a second concentration of said micro-organism greater than said first concentration, the amount of a nutrient selected from at least one of nitrogen and phosphorus introduced into said second vessel being limited such that a substantial proportion of the increase in concentration of said microorganism in said second vessel results from accumulation of poly(β-hydroxybutyric acid).

* * * * *